US008398118B2

(12) United States Patent
Allburn

(10) Patent No.: US 8,398,118 B2
(45) Date of Patent: Mar. 19, 2013

(54) APPARATUS AND METHOD FOR FINGERPRINT CAPTURE

(76) Inventor: David M. Allburn, Glouster, OH (US)

( * ) Notice: Subject to any disclaimer, the term of this patent is extended or adjusted under 35 U.S.C. 154(b) by 820 days.

(21) Appl. No.: 12/188,506

(22) Filed: Aug. 8, 2008

(65) Prior Publication Data

US 2009/0285458 A1 Nov. 19, 2009

Related U.S. Application Data

(60) Provisional application No. 61/002,770, filed on May 15, 2008.

(51) Int. Cl.
*B42D 1/00* (2006.01)
*B42D 19/00* (2006.01)
*B42D 15/00* (2006.01)
*B42D 15/10* (2006.01)

(52) U.S. Cl. .............. 283/78; 281/2; 281/5; 283/61; 283/62; 283/67; 283/68; 283/69; 283/70; 283/72; 283/74; 283/75; 283/81; 283/91; 283/900; 283/901

(58) Field of Classification Search .............. 281/2, 5, 281/51; 283/61, 62, 67, 68, 69, 70, 72, 74, 283/75, 78, 81, 91, 117, 900, 901
See application file for complete search history.

(56) References Cited

U.S. PATENT DOCUMENTS

| 3,675,618 | A | | 7/1972 | Lezak | |
|---|---|---|---|---|---|
| 5,381,487 | A | * | 1/1995 | Shamos | 283/69 |
| 5,546,471 | A | | 8/1996 | Merjanian | |
| 6,357,799 | B1 | * | 3/2002 | Shibata et al. | 283/91 |

* cited by examiner

*Primary Examiner* — Dana Ross
*Assistant Examiner* — Justin V Lewis
(74) *Attorney, Agent, or Firm* — Melanie Martin-Jones

(57) ABSTRACT

A device and method for allowing secure self-capture of multifold fingerprint impressions. The device includes a strip of fingerprint labels wrapped about a tubular ergonomic roller. A subject inserts the thumb of a first hand into the ergonomic roller and grips the roller between his thumb and forefinger. The subject then rolls the inked tip of a finger on his second hand across a label in a first rotational direction while rotating the ergonomic roller in an opposite rotational direction. To prevent fraudulent substitution of fingerprinting materials that are distributed to a subject, the materials are marked with machine readable invisible barcodes that are associated with a unique identification number. After a subject captures his fingerprints and submits his materials to a trusted observer, the barcodes on the materials are compared to the identification number to determine whether the materials submitted are in-fact those that were distributed to the subject.

18 Claims, 8 Drawing Sheets

APPARATUS AND METHOD FOR FINGERPRINT CAPTURE

CROSS-REFERENCES TO RELATED APPLICATIONS (Not Applicable)

This application claims the benefit of U.S. Provisional Application No. 61/002,770 filed Nov. 13, 2007.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

The present invention relates generally to fingerprint capture devices, and more particularly to an ink-on-paper type-4 fingerprint capture device and a method for detecting and thwarting fingerprint substitution fraud.

2. Description of the Related Art

In today's security conscious environment, large numbers of subjects not involved with the criminal justice system need to be fingerprinted efficiently and effectively to facilitate background verification. These subjects include literally millions of individuals seeking employment, individuals seeking professional certifications, volunteers and mentors for churches, 4-H, YMCA, and schools, and millions of other paid workers in numerous professions such as banking, securities, insurance, realty, and many more. Some of these subjects are highly motivated felons indulging a compulsion to molest children or do other harm who readily engage in impersonation and other forms of identity fraud to further their criminal ambitions.

Fingerprints of noncriminal subjects are typically captured by electronically scanning the fingers of the individual, or by making ink impressions of each of the individual's fingers on a standard paper card for electronic scanning at a later time. In either case, the scanned fingerprints are examined to ensure that they are suitable for processing by an Automatic Fingerprint Identification System (AFIS) operated by state law enforcement or Federal Bureau of Investigation (FBI) authorities using type-4 (rolled) or type-14 (flat) impressions. Obtaining fingerprint impressions is termed "capture." Transmitting fingerprints to an AFIS and participating in an AFIS identification process is termed "query." In order to capture sufficiently unique image data from the impression of a subject's finger to perform a type-4 query matching the millions of fingerprints currently on file, more fingertip area is needed than is typically transferred when a subject simply presses their fingertip flat against a paper card or a glass scanner plate as is required for type-14 queries. It is therefore preferable to have a subject roll their fingertip across a fingerprinting medium from one lateral edge of their fingernail to the opposite lateral edge of their fingernail to produce a wider impression that shows more unique fingerprint patterns. AFIS performance is thereby improved and the occurrence of rejecting a fingerprint record due to an insufficient sample, termed "reject rate," is significantly reduced. Even still, well documented FBI reject rates for ink-on-paper type-4 cards are typically on the order of 20%. This means that one in every five persons submitting rolled fingerprints on cards will be asked to submit another card, thereby requiring a subject to return to a fingerprinting site to have his fingerprint's recaptured. In the case of electronic live-scanned fingerprint capture, time spent repeating the scan of a subject's fingers due to insufficient samples can cause substantial delays and can be a serious impediment when attempting to fingerprint a large group of people in a fixed amount of time.

In the past, a problem frequently associated with poor quality rolled fingerprint impressions on paper cards has been that, while rolling a subject's selected finger onto a paper card, the other fingers of the subject on the same hand tend to get in the way, thereby causing the selected finger to squirm or slide which smudges or distorts the fingerprint impression.

Similarly, electronic live capture methods for acquiring fingerprints have been associated with a number of significant disadvantages: they require a costly trained operator; they only capture the prints of one subject at a time; they require expensive equipment; they require subjects to undertake costly and inconvenient travel; subjects typically must wait, often for extended periods of time, at commercial fingerprint service centers or at unaccommodating police booking rooms; and those who administer such live capture methods typically cannot guarantee that the person whose prints they capture is the same individual who was sent to them for that purpose.

Accordingly a need exists for a mechanism and a method for capturing fingerprint impressions that are suitable for AFIS matching from large numbers of live persons simultaneously that can be implemented without the aforementioned disadvantages.

BRIEF SUMMARY OF THE INVENTION

The invention embodies a fingerprinting device, a method for using said device, and an anti-fraud process for facilitating secure, inexpensive, and expeditious capturing and processing of fingerprint impressions for transmission to any Automated Fingerprint Identification System (AFIS), such as those operated by state and federal law enforcement authorities.

The fingerprinting device includes a strip of conventional fingerprint labels, commonly referred to as "retabs," wrapped around the exterior surface of a tubular ergonomic roller that is preferably formed of conventional water pipe insulation or a similar lightweight and flexible material. The strip is preferably removably secured to the roller by a rubber band. To create a type-4 rolled fingerprint impression, the subject partially inserts the thumb of a first hand into the tubular roller and grips the roller between the thumb and forefinger of that hand. The subject then applies the inked tip of a first chosen finger on his second hand to a first fingerprint label on the strip and rolls his finger across the label in a first rotational direction from a first lateral edge of his fingernail to the second lateral edge of his fingernail in smooth, continuous fashion while rotating the roller in an opposite rotational direction with his first hand. Using the same finger, the subject then rolls fingerprints onto each of the remaining fingerprint labels on the same strip in an identical manner while re-inking his finger as often as is necessary. This process is repeated for each of the subject's fingers on both hands, with a different fingerprint strip being fastened to the roller for each finger. To create a type-14 flat impression, the subject presses his fingers flat against the removable media that are supplied in the shape and form called for in the type-14 NIST (National Institute of Standards and Technology) specification.

It is preferred that the tubular roller be slit and scored along its interior surface so that it can be unrolled and flattened into a generally rectangular member. As such, the roller can be stored and shipped in a convenient manner and at a greatly reduced cost as compared to the rolled, tubular form of the roller. To reform the roller for use, a subject simply rolls the flattened member back into a tube and fastens the ends of the member together with adhesive or mechanical fasteners.

To prevent and detect fraud, each of the fingerprint type-4 strips and labels and each of the type-14 strips and labels, as well as preferably several other items that are distributed to a subject as part of a fingerprinting packet, are marked with machine readable, invisible barcodes that are associated with a unique, predetermined identification number. Thus, if a subject were to surreptitiously substitute fraudulently prepared strips or fingerprint labels for those that were provided to him, such fraud would be easily detected by scanning and comparing the barcodes on the various materials with the identification number. Since the barcodes are invisible, a subject will generally be unaware of their presence and will therefore be less likely to tamper with them. It is preferred that non-functional visible barcodes be printed on the fingerprinting materials in addition to the invisible barcodes to serve as a "red-herring," thereby further reducing the likelihood that a subject will look for or gain awareness of the functional invisible barcodes.

The claimed fraud resistant process includes capturing a subject's fingerprint impressions at a convenient site, such as at a place of business or a meeting hall, protection of the impressions using standard chain-of-custody methods, and processing of those impressions off-site at a central laboratory, which includes scanning and comparing the invisible barcodes described above as well as the selection of best-of-breed impression samples for each finger. The processed impressions are thereafter transmitted to an AFIS in the form of a query.

It is therefore an object of the present invention to provide multifold, high quality, rolled ink-on-paper fingerprint impressions for subsequent processing. This overcomes the problem of traditionally high FBI rejection rates because the best finger impressions from several available can be selected for each finger for submission to an AFIS. This significantly improves the chances that a complete resulting fingerprint record comprised of only such best-of-breed specimen impressions will be found, in its entirety, to be of acceptable quality, thereby eliminating the need for subjects to return to a fingerprinting site to recapture any impressions.

It is another object of the present invention to simultaneously and expeditiously capture rolled fingerprints from groups of size limited only by the seated desk space available at a particular fingerprinting facility. For example, a large classroom of 100 people who complete their fingerprint capture simultaneously in twenty minutes total time (shown to be typical of this invention) implies a throughput rate of three hundred (300) persons per hour.

It is another object of the present invention to facilitate subjects making their own multifold, high quality, rolled fingerprint impressions for each finger without requiring a trained operator to physically manipulate the subject's fingers or operate complicated electronic equipment. This overcomes the high cost associated with all other classes of fingerprint capture methodology based on electronic live-scan capture, which uniformly require a paid trained operator.

It is another object of the present invention to facilitate convenient and expedited self capture of high quality, rolled fingerprint impressions via a device that utilizes a motion that is natural for most subjects, such as the motion made when a person wrings the water from a wet towel by twisting the ends of the towel in opposite directions. This eliminates the need for training subjects and overcomes the problem of a subject's unselected fingers creating an obstruction while the subject is capturing the print of a selected finger.

An additional object of the present invention is to provide a disposable, self-capture fingerprinting device that can be easily constructed using inexpensive, commercially available materials. Such a device can be provided through office supply stores, notaries public, or resellers in the background screening or drug testing industries. This eliminates the need for employers to invest in high cost electronic live-scan capture systems that require special facilities and skilled operators, and which are limited to one-subject-at-a-time processing.

Yet another object of the present invention is to facilitate local, on-site fingerprint capture at convenient offices or branch locations where subjects already work or visit to apply for employment or volunteering, or other sites where subjects convene for efficient group training and qualification purposes and not necessarily for the sole purpose of capturing fingerprints. This overcomes the inconvenience of having to visit distant central fingerprint service centers, and eliminates the distasteful prospect of having to visit police booking rooms.

Another object of the present invention is to control the potential for imposter fraud that is inherent to all fingerprint capture systems that require a subject to depart from the view of an interviewer, employer, or other trusted observer, and travel to a distant site such as a central fingerprint service center or a police booking room to have their fingerprints captured by individuals who are not previously acquainted with the subject. Highly motivated subjects, such as pedophiles and career felons who conceal their disqualifying offenses and who intend to infiltrate staffs and agencies for criminal purposes, can and do hire imposters and equip them with convincing credentials that pass the casual inspection afforded by paid operators of live-scan systems and even busy law enforcement officers. This type of fraud results in the fingerprints of a third party, who the applicant had corrupted and conspired with for the purpose of deception, being captured and submitted to the AFIS under the name of the applicant. The present invention overcomes this problem by conducting the fingerprint capture in full view of the employer's human resources official or another appointed trusted observer, such as a notary public, who is brought to the venue for authentication purposes. This direct observation prevents imposter fraud and establishes a credible chain of custody so that the fingerprint impressions are not vulnerable to tampering after they have been captured.

A final object of the present invention is to prevent and expose substitution fraud by individuals who attempt to surreptitiously substitute prepared fingerprinting materials for those that are provided to them. This is accomplished by printing machine-readable, invisible barcodes on all the media that will contain or receive a subject's fingerprint impressions, thereby rendering the various materials fully accountable and unique. Any substitution of the materials is therefore detectable upon inspection and comparison of the barcodes with a unique, predetermined identification number.

BRIEF DESCRIPTION OF THE SEVERAL
VIEWS OF THE DRAWINGS

Figure 1:
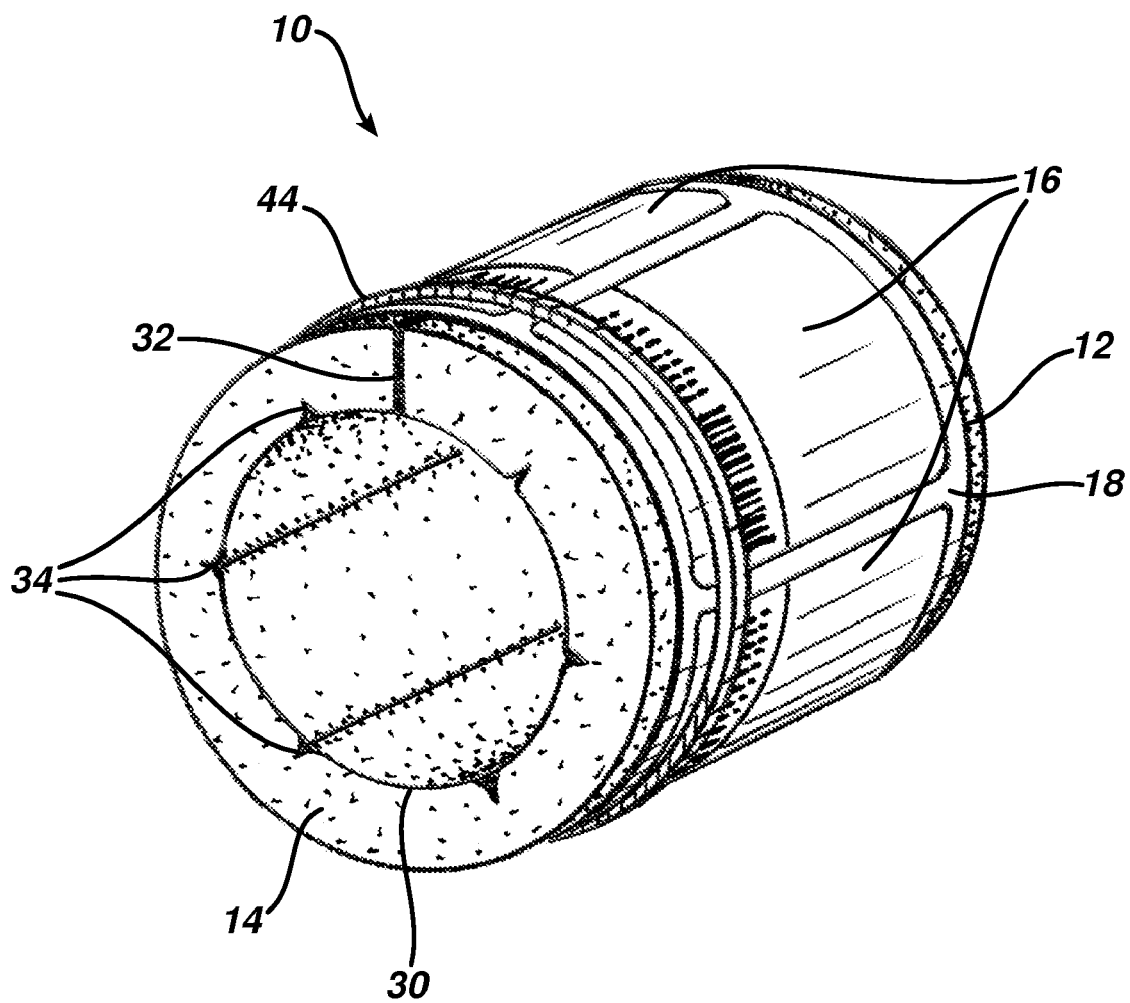
FIG. 1 is a perspective view illustrating the preferred embodiment of the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DETAILED DESCRIPTION OF THE INVENTION

Figure 2:
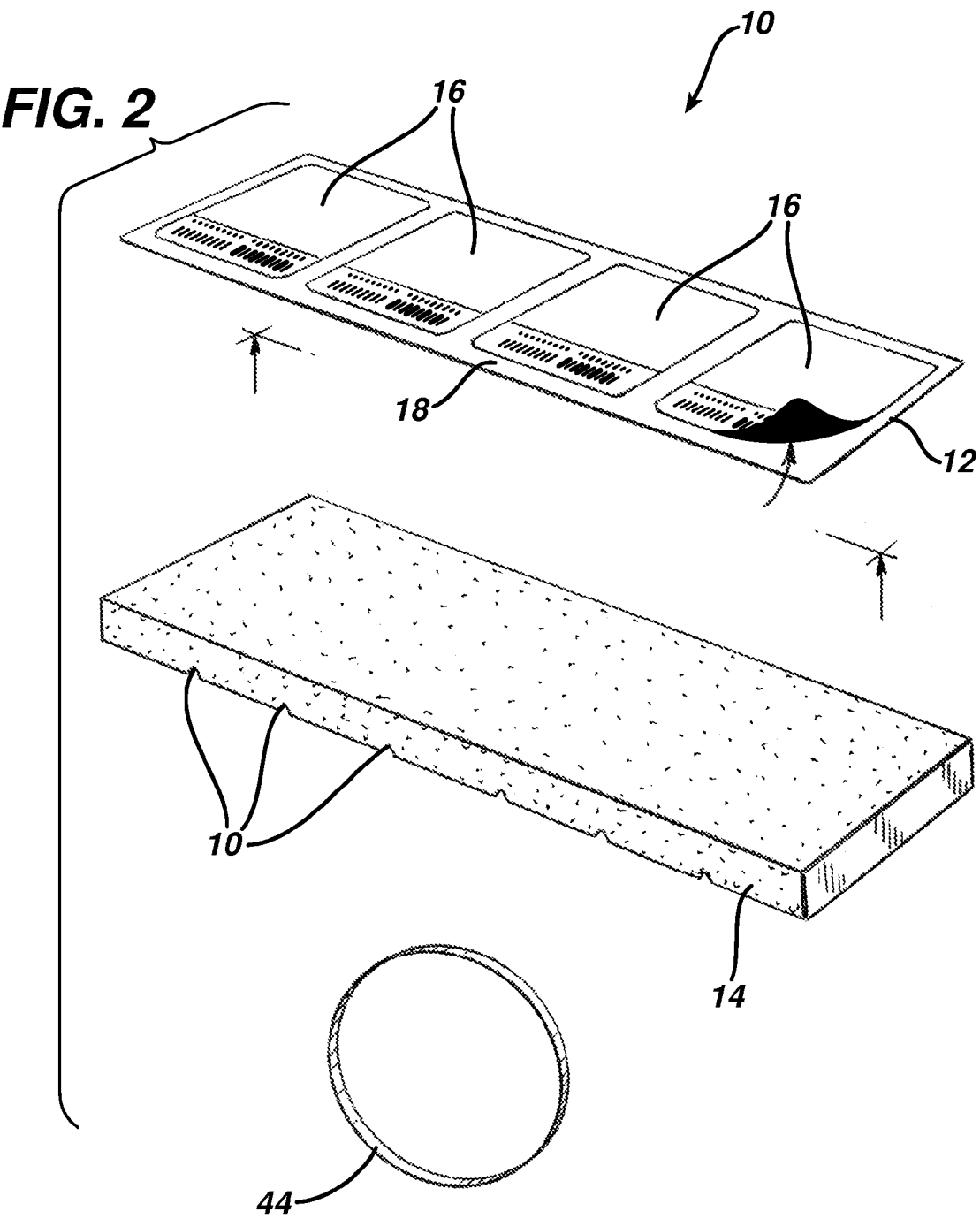
FIG. 2 is an exploded view in perspective illustrating the preferred embodiment of the present invention shown in FIG. 1 in a flattened form.

Referring to FIGS. 1 and 2, a fingerprinting device 10 in accordance with the present invention is illustrated. The device 10 is provided for allowing a subject to quickly and easily produce multifold, high quality rolled fingerprints at relatively low cost. The device 10 generally includes, in combination, a fingerprint strip 12 wrapped about an ergonomic roller member 14. The separate components of the inventive device 10 will now be described in-turn, with a discussion of the complete device 10 and a method for its use to follow.

Referring specifically to FIG. 2, the fingerprint strip 12 is cut from a conventional roll of finger print labels of a type that will be familiar to those skilled in the art. The fingerprint strip 12 preferably includes four conventional adhesive-backed fingerprint labels 16 (commonly referred to as "retabs") that are removably mounted to a waxed or otherwise substantially low adhesion medium, such as the mounting strip 18. Each of the labels 16 measures about 1.5 inches square. Labels having other shapes and/or dimensions are contemplated, although it is generally required that each label have a fingerprintable area that measures at least about 1 inch square for acquiring a fingerprint of sufficient size for processing by an AFIS. The front surface of each label is chemically treated to quickly absorb and retain special purpose fingerprint ink from a subject's fingers. The rear surface of each label is generally opaque for reducing the likelihood that any marks or debris that may be on the rear surface of a label, or behind a label, will be visible through the front surface of the label, thereby increasing the likelihood that the label will yield a well-defined, usable fingerprint. Although the preferred embodiment of the invention incorporates fingerprint labels of the type described above, it is to be understood that any other conventional fingerprinting media, including the coated inkless variety, can alternatively be used.

Figure 3:
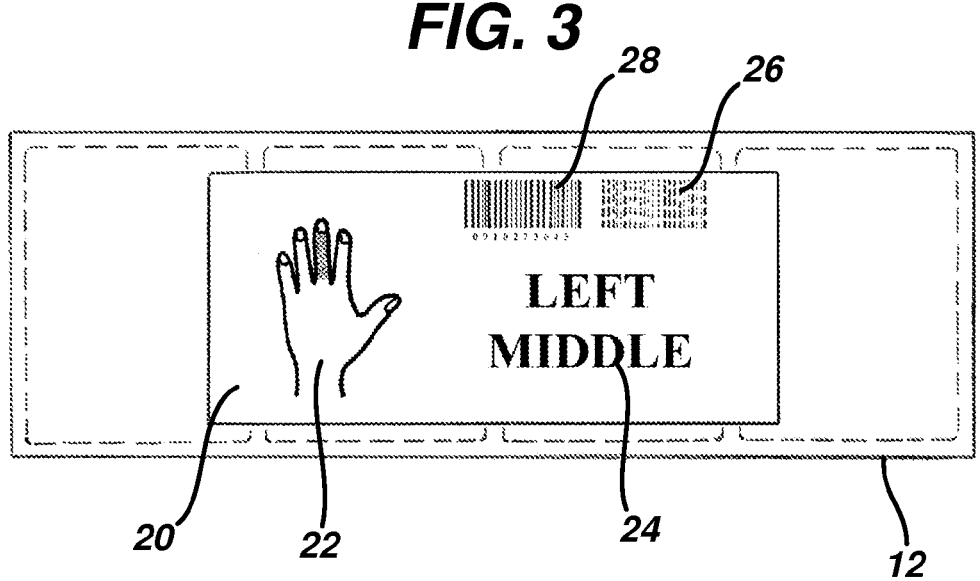
FIG. 3 is a rear view illustrating the instructional label of the preferred embodiment of the present invention shown in FIG. 1.

Referring now to FIG. 3, an instructional label 20 is provided on the reverse side of the fingerprint strip 12 for indicating to a subject which finger the fingerprint strip 12 should be used to acquire prints from, and for indicating to a subsequent examiner and/or processing agent which fingerprints have been recorded on the fingerprint labels 16 of the fingerprint strip 12. For example, the instructional label 20 illustrated in FIG. 3 indicates that the fingerprint strip 12 should be (or has been) used to record fingerprints from the middle finger of a left hand. For clarity, the instructional label 20 of the preferred embodiment of the invention incorporates both a graphic indicium 22 and a text indicium 24, although it is contemplated that the label 20 can have one and not the other. It is further contemplated that any other type of indicia, such as numbers or color codes, can additionally or alternatively be incorporated on the instructional label 20 for designating a particular finger. It is still further contemplated that text indicia on the instructional label 20 can be provided in multiple languages.

Figure 4A:
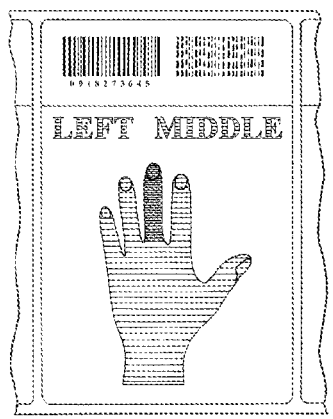
FIG. 4a is a front view illustrating a fingerprint label of an alternative embodiment of the present invention with instructional indicia printed thereon in non-reproducible blue ink.
Figure 4B:
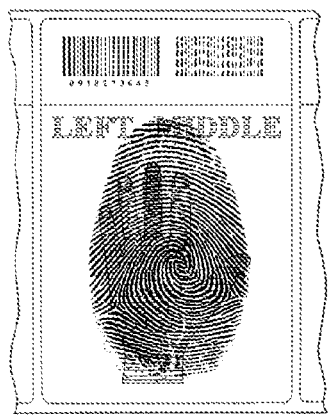
FIG. 4b is a front view illustrating the fingerprint label of FIG. 4a with a fingerprint impression imprinted thereon.

Although it is preferred that the graphic and text instructional indicia 22 and 24 be printed in conventional black ink on the instructional label 20 on the rear of the fingerprint strip 12, it is contemplated that similar instructional indicia can alternatively or additionally be printed directly on the fingerprintable area of a fingerprint label in conventional non-reproducible blue ink, as shown in FIGS. 4a and 4b. The non-reproducible ink is visible to the human eye but is not visible to conventional photo scanners of the type used to scan fingerprints. The fingerprint shown in FIG. 4b would therefore be read by an electronic scanner as though the instructional indica shown were not present.

Figure 5:
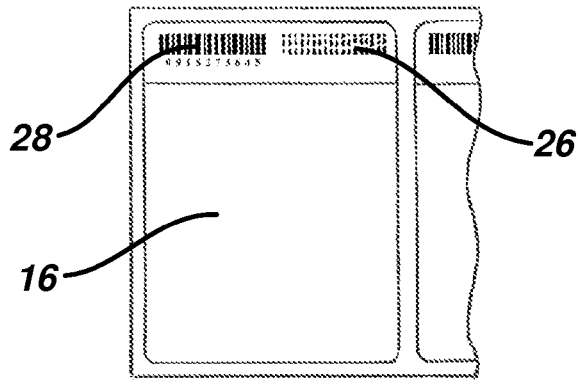
FIG. 5 is a front view illustrating a fingerprint label of the preferred embodiment of the present invention.

Referring to FIGS. 3 and 5, special machine-readable, invisible barcodes 26 (i.e., invisible to the human eye) are printed on the instructional label 20 and on each of the fingerprint labels 16, as well as on various other components of a fingerprinting packet (described below) that are distributed to a subject for facilitating the prevention and detection of certain forms of fraud. The barcodes 26 allow the components of a fingerprinting packet to be associated with one another and with a unique, predetermined identification number that is issued to each subject, thereby allowing detection of fraudulent substitution of any of the packet's components. For example, an unscrupulous subject may bring fraudulently prepared fingerprint strips (e.g., strips that have been stolen from a previous fingerprinting session that were subsequently marked with the fingerprints of a cooperative individual who does not have a problematic criminal history) with him to a fingerprinting session. When others are not watching, the subject may substitute the prepared strips for the provided strips with the hope of being matched with the cooperative individual's clean history. In another example, two individuals working in collusion, one with a problematic background and one with a clean background, may sit next to one another at a fingerprinting session. When others are not watching, the individual with the clean background may pass his already-marked fingerprint strips to the individual with the problematic background while the individual with the problematic background passes blank fingerprint strips to the individual with the clean background to be marked. In this manner, both individuals would normally be matched with a clean history if the exchange were successful.

With the invisible barcodes 26 in place, however, the fingerprint labels 16, instructional label 20, and other components of the subject's fingerprinting packet can be scanned by a machine and compared to the subject's unique, predetermined identification number after being collected from the subject. If it is found that the barcodes on the instructional label 20 or fingerprint labels 16 do not match the identification number, or if it is found that the instructional label 20 or fingerprint labels 16 do not have barcodes on them, then fraud will likely have been detected and appropriate action can be taken.

Since the barcodes 26 are invisible, a subject who engages in substitution fraud will generally be unaware of the barcodes' existence and will therefore be unable to alter or reproduce the barcodes 26. As an additional security feature, it is preferred that visible barcodes 28 be printed on the fingerprint labels 16, the instructional label 20, and on the other components of a fingerprinting kit in addition to the invisible barcodes 26 to serve as a "red herring." That is, the visible barcodes 28 are not functional for their traditional purpose of identification, but are instead included to mislead those who wish to perpetrate substitution fraud by causing them to believe that the visible barcodes 28 are indeed genuine, thereby making it more likely that they would tamper with or attempt to reproduce the visible barcodes 28 and less likely that they would look for, or otherwise gain awareness of, the invisible barcodes 26. It is contemplated that the invisible barcodes 26 can be entirely omitted, and that only traditional visible barcodes can be used to associate and reference the various components of a fingerprinting packet. It is further contemplated that the visible barcodes 28 can alternatively be printed on the fingerprintable area of the fingerprint labels 16 in non-reproducible blue ink in the same manner as the instructional indicia described above. It is still further contemplated that the invisible barcode 26 that is printed on the instructional label 20 can alternatively be printed directly on the mounting strip 18.

Referring back to FIG. 1, the ergonomic roller member 14 is a generally tubular body having a central thumb channel 30. The roller 14 is preferably formed of a segment of conventional home water pipe insulation. It is contemplated that the roller can be formed of any other suitably durable and lightweight material, including, but not limited to rubber, plastic, wood, aluminum, other types of foam, or various composites, although standard water pipe insulation is preferred for its low cost and wide commercial availability.

The roller 14 preferably has a length of about 2.5 inches, an inner diameter of about 1.25 inches, and an outer diameter of about 2 inches. Rollers having other dimensions are contemplated, although the roller should generally be at least 2.5 inches long to provide a sufficient grip-margin (described in greater detail below), with an outer diameter of at least 2 inches to allow for accommodating a fingerprint strip of sufficient length, and an inside diameter of at least 1 inch to allow the largest likely thumb of a subject to fit comfortably inside the thumb channel 30. It is further contemplated that the roller 14 can have a variety of alternative exterior cross-sectional shapes, such as octagonal, rectangular, or triangular, although a roller with a circular exterior cross-section is highly preferred from an ergonomic standpoint.

Referring to FIGS. 1 and 2, the roller 14 is slit along a longitudinal slit line 32 and is scored along several radially disposed longitudinal score lines 34 that are formed in the roller's interior surface. The slit and the scoring allow the roller 14 to be unrolled and substantially flattened into a generally planar, rectangular member, as shown in FIG. 2. The roller 14 is preferably packaged, shipped, and stored in its flattened form in order to conserve space, simplify handling, and reduce mailing costs, as packages that are bulbous or irregularly shaped generally cannot be processed by U.S. Postal Service machinery and are therefore more expensive to mail. Low mailing costs are also facilitated by the relatively low weight of the foam insulation that the roller 14 is made from. While it is preferred that the roller 14 be slit, scored, and flattened in the manner described above, it is contemplated that the roller 14 can alternatively be provided in a wholly intact, tubular form without being slit, scored, or flattened.

Figure 6A:
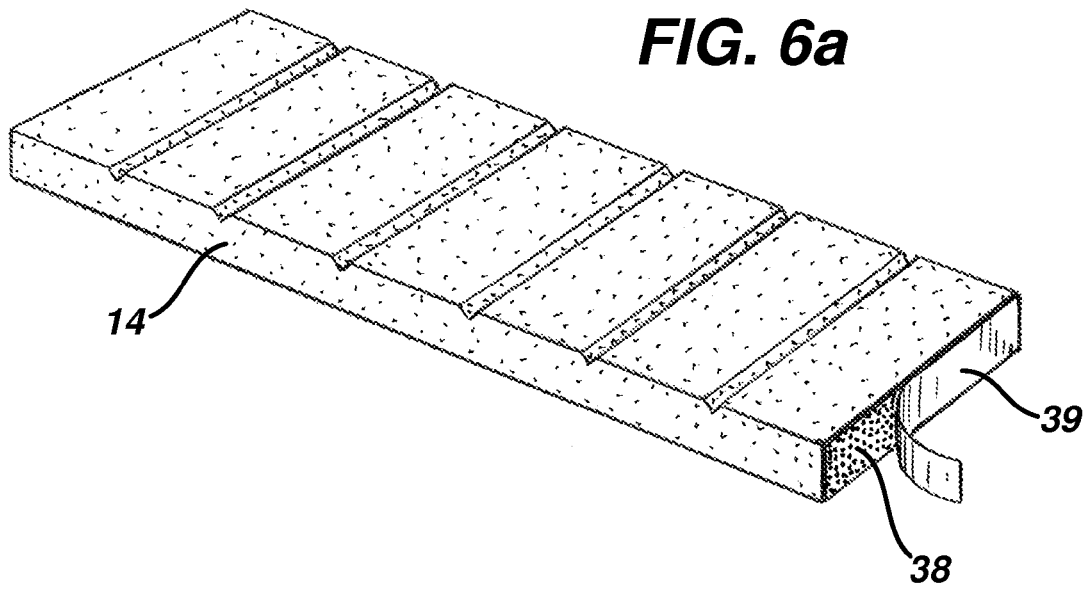
FIG. 6a is a perspective view illustrating the ergonomic roller member of the preferred embodiment of the present invention shown in FIG. 1 in a flattened form.
Figure 6B:
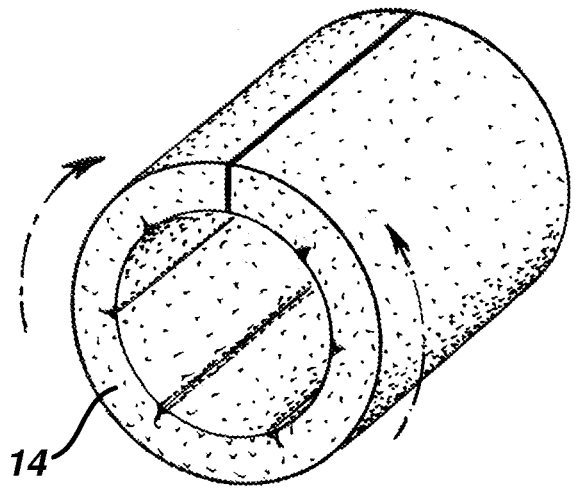
FIG. 6b is a perspective view illustrating the ergonomic roller member of the preferred embodiment of the present invention shown in FIG. 1 in a tubular form.

Referring now to FIG. 6a, the ends of the flattened roller 14 (only one end is within view, but both ends are substantially identical) are each coated with a layer of adhesive 38, such as contact cement, which is in-turn covered with a strip of wax paper 39 or other generally non-adhering material to preserve the adhesive 38 and to prevent the ends from sticking to other objects. When a subject is ready to use the roller 14, the subject removes the wax paper 39 from the ends of the roller 14, thereby exposing the adhesive. The subject then rolls the roller 14 inwardly upon itself and brings the ends together to form a tube, as shown in FIG. 6b. The adhesive 38 thereafter holds the ends of the roller 14 together and maintains the roller's tubular shape. Depending on the type of adhesive used, the subject may be required to hold the ends of the roller 14 together for a short time to allow the adhesive to form a sufficient bond. Although adhesive is preferred for holding the ends of the roller 14 together, it is contemplated that any other fastening means may be used to secure the roller 14 in its assembled, tubular form, including, but not limited to tape, staples, pins, or rubber bands.

Figure 7A:
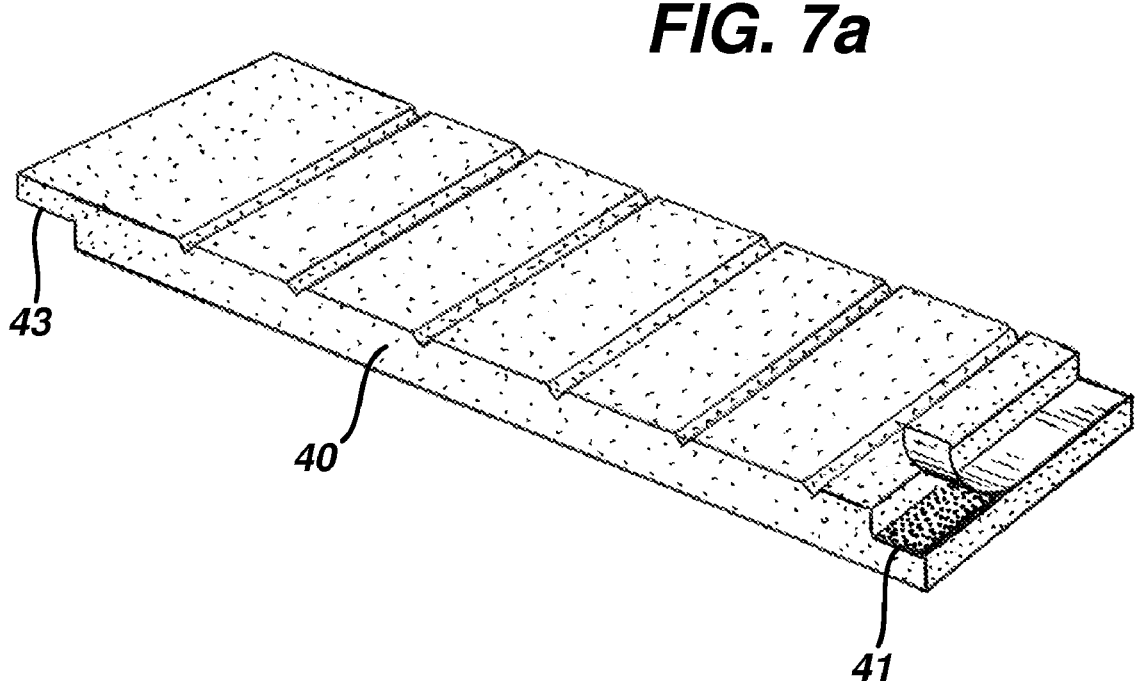
FIG. 7a is a perspective view illustrating an ergonomic roller member of an alternative embodiment of the present invention in a flattened form.
Figure 7B:
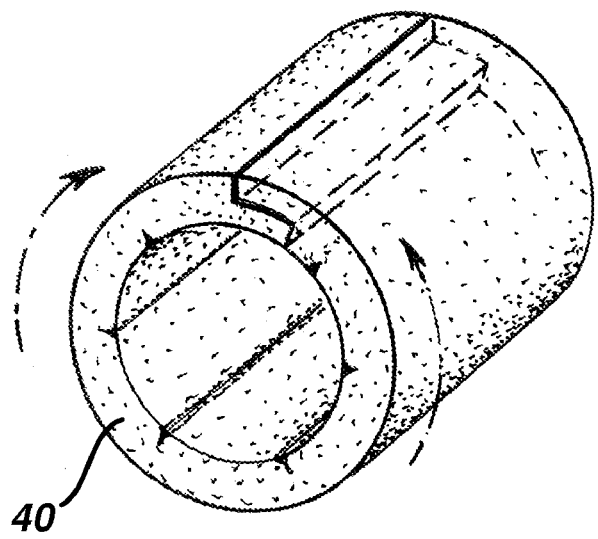
FIG. 7b is a perspective view illustrating the ergonomic roller member of FIG. 7a in a tubular form.

Referring to an alternative embodiment of the invention shown in FIGS. 7a and 7b, it is contemplated that the ends of the roller 40 can be formed with complementary notches 41 and 43 to increase the amount of contacting surface area between the ends when they are brought together, thereby increasing the strength of the adhesive bond between the ends. It should be understood that the alternative embodiment in FIGS. 7a and 7b is shown by way of example only, and that the ends of the roller can be formed in a variety of different ways to increase surface-to-surface contact between the ends without departing from the spirit of the invention.

Once the ergonomic roller 14 has been assembled into its tubular form, a subject then wraps the fingerprint strip 12 around the curved outer surface of the roller 14 with the finger print labels 16 facing outwardly, as illustrated in FIG. 1. The fingerprint strip 12 is then removably secured to the roller with a rubber band 44 that is placed around the outer surface of the fingerprint strip 12. The rubber band 44 should be positioned adjacent a lateral edge of the mounting strip 18 to prevent the band 44 from blocking the fingerprintable area of the fingerprint labels 16. Although a rubber band is preferred for its low cost and ease of use, all other methods for temporarily securing the fingerprint strip 12 to the ergonomic roller 14, such as with tape, adhesives, or pins, are contemplated. With the fingerprint strip 12 fastened to the roller 14, the inventive device 10 is complete and is ready to be used to record a subject's fingerprint impressions.

Generally, when an employer, agency, or other administering entity uses the inventive device 10 to obtain fingerprints, a subject or group of subjects whose fingerprints are to be acquired will be congregated at a place of work or other convenient meeting place and will be seated in an orderly, classroom-style arrangement. A trusted observer (i.e., an administrative professional, volunteer, notary, or other trusted person tasked with collecting the subjects' fingerprints) will then distribute a fingerprinting packet (not shown) to each subject. Each packet typically includes an envelope that contains at least a flattened ergonomic roller of the type described above, at least one fingerprint strip of the TWO TYPES described above, for each of a subject's fingers that is to be fingerprinted, and a rubber band. Other items that are preferably provided as part of the fingerprinting packet include a personal data form to be filled in by the subject, a standard FBI ten-print card for affixing best-of-breed fingerprint labels to, a sealed ink sandwich, a sealed moist towel for allowing a subject to clean ink from his fingers, and specially sized and marked fingerprint labels not requiring use of the ergonomic roller for capturing multiple specimens of AFIS-required "flat slap" impressions (type-14).

After receiving the fingerprinting packets, the subjects can optionally be shown a brief instructional video demonstrating how to utilize the contents of the packet to record their fingerprints. Alternatively, the subjects may receive live instruction from a trained individual, or, as a further alternative, an instructional sheet, pamphlet, or manual may be included in the fingerprinting packet for illustrating and/or describing the proper method of using the fingerprinting materials.

Figure 8:
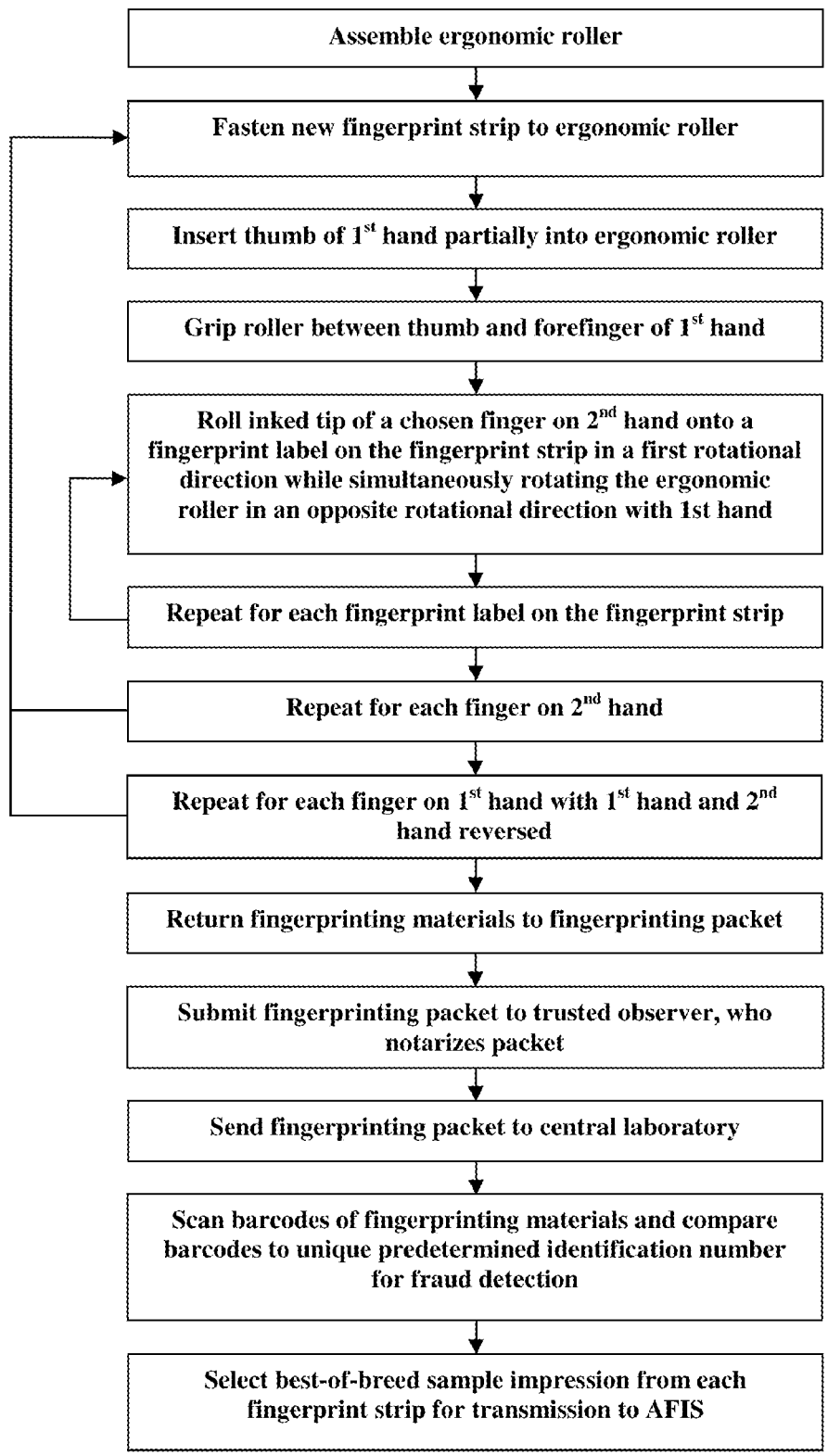
FIG. 8 is a flowchart setting forth a method for capturing, processing, and submitting a subject's fingerprint impressions.
Figure 9:
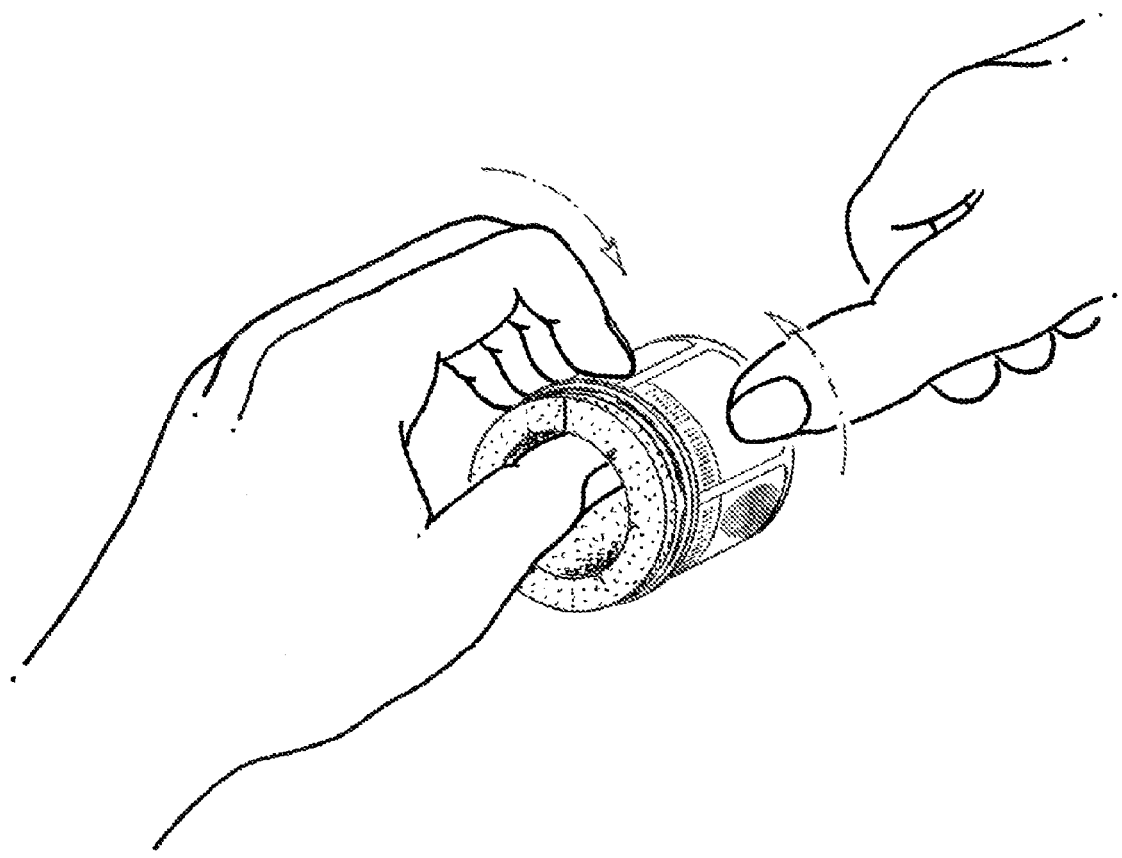
FIG. 9 is a perspective view illustrating the preferred embodiment of the present invention shown in FIG. 1 being used by a subject to capture fingerprint impressions.
Figure 10A:
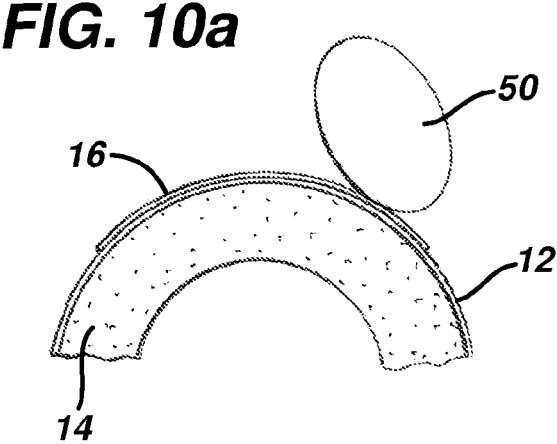
FIGS. 10a-10c are a sequence of partial cross-sectional views illustrating the relative rotational motion of the preferred embodiment of the present invention and a subject's finger when capturing a fingerprint impression.
Figure 10B:
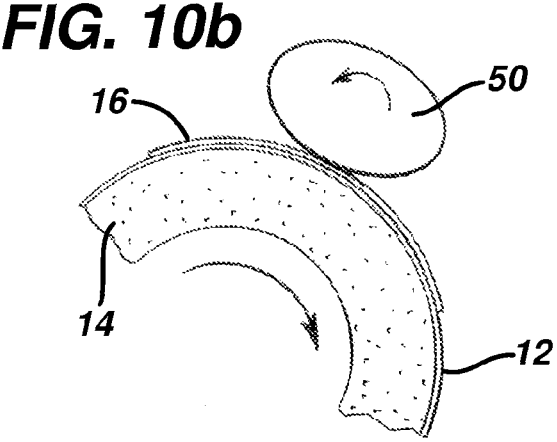
Figure 10C:
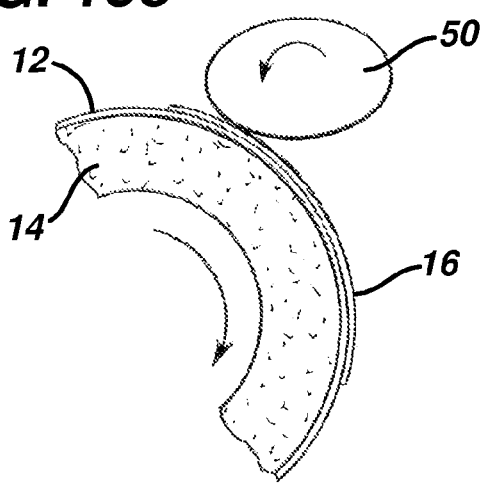

Referring now to the flowchart shown in FIG. 8, a typical step-by-step process for using the inventive device to acquire the fingerprints of a subject, or, more likely, a multitude of subjects simultaneously, is set forth. First, a subject assembles the inventive device in the manner described above, with a first fingerprint strip fastened to the ergonomic roller for acquiring fingerprints from a first chosen finger of a first hand. The subject then partially inserts the thumb of his second hand into the thumb channel of the ergonomic roller and grips the roller between the thumb and forefinger of his second hand without touching or blocking the fingerprint labels on the fingerprint strip, as shown in FIG. 9. Referring to the sequence of cross-sectional views shown in FIGS. 10a-10c, the subject then applies the inked tip of his first chosen finger 50 to a first fingerprint label 16 on the fingerprint strip 12 and rolls his finger across the label 16 in a first rotational direction from a first lateral edge of his fingernail to the second lateral edge of his fingernail in smooth, continuous fashion while rotating the ergonomic roller 14 in an opposite rotational direction with his second hand. By producing a natural motion similar to that made when wringing a washcloth, the subject thereby easily transfers a high quality, rolled specimen impression of his chosen finger 50 onto the first fingerprint label. Using the same finger, the subject then rolls fingerprints onto each of the remaining fingerprint labels on the same fingerprint strip in an identical manner while re-inking his finger as often as is necessary (see FIG. 9).

After the subject has marked each of the fingerprint labels on the first fingerprint strip with his first chosen finger, the subject then removes the first fingerprint strip from the ergonomic roller and replaces it with a second fingerprint strip for acquiring prints from a second chosen finger. Using his second chosen finger, the subject then rolls fingerprints onto each of the fingerprint labels of the second fingerprint strip in a manner identical to that described above. The subject repeats this process for each finger on each hand.

After the subject has captured impressions from all of his fingers (including type-14 flat-slap impressions, if they are required), the subject returns the fingerprinting materials (including his multi-fold captured impressions) to the fingerprinting packet within view of the trusted observer and signs to attest the impressions are the subject's alone and no other's. The subject then relinquishes custody of the packet to the trusted observer, thereby establishing a dependable chain of custody. The observer then seals the packet and attests in writing, such as with a notarial emboss on the packet, that the print impressions captured are indeed those of the person making application.

Finally, as part of the chain of custody initiated by the trusted observer who took possession of the print impressions, said trusted observer sends the fingerprinting packet to a central processing laboratory. The laboratory selects, either manually or by computerized electronic means, the best-of-breed fingerprint impressions from each fingerprint strip for compositing into a superior collection of impressions on a hard-copy or virtual standard FBI ten-print card, then formats, scans, and digitizes said composited impressions into a type-4 or type-14 conforming digital file suitable for query to state or federal Automatic Fingerprint Identification Systems (AFIS). Additionally, the laboratory scans the invisible barcodes (described above) on the various components of the fingerprinting packet and compares them to a unique, predetermined identification number to check for any substitution fraud that may have taken place. The laboratory then initiates a query by transmitting the digital fingerprint file to the AFIS. The query generally results in an official AFIS response that is handled and disseminated according to various federal and state laws applicable to the query's permitted purpose, as will be appreciated by those skilled in the art.

Optionally, it is contemplated that further authentication of a subject's fingerprints can be attained by having the subject place an enrollment phone call to a voiceprint service contractor, who then captures a digital voiceprint of the subject's vocalizations for inclusion with the subject's archived fingerprint record. This enables real time authentication of a subsequent request, allegedly by the subject, for his fingerprint record to be retrieved and re-submitted to another AFIS for a different permissible purpose.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A device for self-capturing fingerprint impressions from a subject's fingers comprising: (a) a tubular ergonomic roller; and (b) multiple fingerprint strips, each strip removably fastened to an exterior of the ergonomic roller and comprising a plurality of peel and stick labels, each label shaped for receipt of a single fingerprint impression when the roller is rotated about a horizontal axis in contact with a first finger and for placement on a ten-print fingerprint document, a given strip capturing multiple impressions of the same fingerprint of the subject when a strip for that finger is fastened to the roller, the labels selectively removed from the strips after the impressions are captured and placed on the fingerprint document.

2. The device for capturing fingerprint impressions set forth in claim 1, wherein the tubular ergonomic roller is formed of a generally rectangular flexible member that is rolled into a tubular shape.

3. The device for capturing fingerprint impressions set forth in claim 1, wherein the labels are removed from the strips and added to the document by at least one of one of detachment and adhesion and digitizing.

4. The device for capturing fingerprint impressions set forth in claim 1, further comprising at least one barcode disposed on the fingerprint strip.

5. The device for capturing fingerprint impressions set forth in claim 4, wherein said at least one barcode is invisible to the human eye.

6. A device for self-capturing fingerprint impressions from a subject's fingers comprising: (a) a tubular ergonomic roller formed of a generally rectangular flexible member that is rolled into a tubular shape; and (b) multiple fingerprint strips, each strip removably fastened to an exterior of the ergonomic roller and comprising a plurality of peel and stick labels, each label shaped for receipt of a single fingerprint impression and for placement on a ten-print fingerprint document, a given strip capturing multiple impressions of the same fingerprint of the subject when a strip for that finger is fastened to the roller and the roller is rotated about a horizontal axis in contact with that finger; and (c) at least one barcode disposed on the fingerprint strip; wherein, after capture, the labels are selectively removed from the strips and placed on the fingerprint document.

7. The device for capturing fingerprint impressions set forth in claim 6, wherein the labels are removed from the strips and added to the document by at least one of one of detachment and adhesion and digitizing.

8. The device for capturing fingerprint impressions set forth in claim 6, wherein said at least one barcode is invisible to the human eye.

9. A method for self-capturing multiple fingerprint impressions with the fingerprinting device of claim 6, the method comprising: (a) wrapping a first fingerprint strip around the exterior of the ergonomic roller and removably fastening the first fingerprint strip thereto; (b) the subject: i) partially inserting a thumb of a first hand into a central channel of the ergonomic roller member; ii) gripping the ergonomic roller between the thumb and a forefinger of the first hand; iii) rolling an inked tip of a first finger of a second hand onto one of said plurality of fingerprint labels in a first rotational direction while simultaneously rotating the ergonomic roller in an opposite rotational direction with the first hand; iv) repeating the step of rolling the inked tip of the first finger using each of the other of said plurality of fingerprint labels on that strip; and (c) removing the fingerprint strip from the ergonomic roller.

10. The method for capturing fingerprint impressions set forth in claim 9, further comprising repeating the method using each other finger on both hands with a next fingerprint strip used for each finger.

11. The method for capturing fingerprint impressions set forth in claim 10, further comprising selecting a best impression from the fingerprint strip for each finger for transmission to an automatic fingerprint identification system.

12. The method for capturing fingerprint impressions set forth in claim 10, further comprising: (a) scanning each of the barcodes; and (b) comparing the barcodes to a predetermined identification number to determine whether any of the fingerprint labels or strips have been fraudulently substituted.

13. A method for preventing and detecting fraudulent substitution of fingerprint impressions captured using the device of claim 6, the method comprising: (a) scanning each of the barcodes; and (b) comparing the barcodes to a predetermined identification number to determine whether any of the fingerprint labels or strips have been fraudulently substituted.

14. The method for preventing and detecting fraudulent substitution of claim 13 wherein the barcode is invisible to the human eye.

15. The device of claim 1 wherein the labels are chemically treated.

16. The device of claim 1 wherein the labels are coated for inkless capture of the fingerprint impressions.

17. The device of claim 6 wherein the labels are coated for inkless capture of the fingerprint impressions.

18. A method for self-capturing multiple fingerprint impressions with the fingerprinting device of claim 17, the method comprising: (a) wrapping a first fingerprint strip around the exterior of the ergonomic roller and removably fastening the first fingerprint strip thereto; (b) the subject: i) partially inserting a thumb of a first hand into a central channel of the ergonomic roller member; ii) gripping the ergonomic roller between the thumb and a forefinger of the first hand; iii) rolling a tip of a first finger of a second hand onto one of said plurality of fingerprint labels in a first rotational direction while simultaneously rotating the ergonomic roller in an opposite rotational direction with the first hand; iv) repeating the step of rolling the tip of the finger using each of the other of said plurality of fingerprint labels on that strip; (c) removing that fingerprint strip from the ergonomic roller; and (d) repeating the steps above for each other finger on both hands using a next fingerprint strip for each other finger.

* * * * *